US011771563B2

(12) United States Patent
Wilga et al.

(10) Patent No.: US 11,771,563 B2
(45) Date of Patent: Oct. 3, 2023

(54) ARTIFICIAL TESSELLATED IMPLANTS, AND SYSTEMS AND METHODS OF MAKING AND USING SAME

(71) Applicant: UNIVERSITY OF ALASKA ANCHORAGE, Anchorage, AK (US)

(72) Inventors: Cheryl Wilga, Anchorage, AK (US); Evelina Natekin, Anchorage, AK (US); Matthew Calhoun, Anchorage, AK (US); Petra Ditsche, Anchorage, AK (US); Raghu Srinivasan, Anchorage, AK (US)

(73) Assignee: UNIVERSITY OF ALASKA ANCHORAGE, Anchorage, AK (US)

(*) Notice: Subject to any disclaimer, the term of this patent is extended or adjusted under 35 U.S.C. 154(b) by 241 days.

(21) Appl. No.: 16/733,639

(22) Filed: Jan. 3, 2020

(65) Prior Publication Data

US 2020/0214848 A1    Jul. 9, 2020

Related U.S. Application Data

(60) Provisional application No. 62/902,752, filed on Sep. 19, 2019, provisional application No. 62/787,923, filed on Jan. 3, 2019.

(51) Int. Cl.
*A61F 2/44* (2006.01)
*A61F 2/30* (2006.01)

(52) U.S. Cl.
CPC .......... *A61F 2/442* (2013.01); *A61F 2/30942* (2013.01); *A61F 2002/30014* (2013.01); *A61F 2002/30069* (2013.01); *A61F 2002/30113* (2013.01); *A61F 2002/30143* (2013.01); *A61F 2002/30153* (2013.01); *A61F 2002/30985* (2013.01)

(58) Field of Classification Search
CPC ................. A61F 2/442; A61F 2/30942; A61F 2002/30985; A61F 2002/30113; A61F 2002/30069; A61F 2002/30014; A61F 2002/30153; A61F 2002/30143; A61F 2/30756; A61F 2002/4495; A61F 2/3094; A61F 2/2875; A61F 2/30965
See application file for complete search history.

(56) References Cited

U.S. PATENT DOCUMENTS

| | | | |
|---|---|---|---|
| 7,655,047 B2 * | 2/2010 | Swords | A61F 2/30965 623/23.54 |
| 2008/0183292 A1 * | 7/2008 | Trieu | A61F 2/442 623/17.11 |
| 2016/0001027 A1 * | 1/2016 | Akervall | A63B 71/085 128/862 |
| 2017/0239054 A1 * | 8/2017 | Engstrand | A61F 2/30965 |

* cited by examiner

*Primary Examiner* — Brian A Dukert
(74) *Attorney, Agent, or Firm* — BALLARD SPAHR LLP

(57) ABSTRACT

A synthetic material can comprise a plurality of rigid components. Each rigid component can be spaced from each adjacent rigid component to define respective interstices between each rigid component and each adjacent rigid component. A flexible material can be disposed within each respective interstice and can extend between and connect to adjacent rigid components.

20 Claims, 15 Drawing Sheets

ARTIFICIAL TESSELLATED IMPLANTS, AND SYSTEMS AND METHODS OF MAKING AND USING SAME

CROSS-REFERENCE TO RELATED APPLICATIONS

This patent claims priority to and the benefit of U.S. Provisional Patent Application No. 62/902,752, filed Sep. 19, 2019, and U.S. Provisional Patent Application No. 62/787,923, filed Jan. 3, 2019, the entireties of which are hereby incorporated by reference herein.

FIELD

This application relates generally to composite materials and, in particular, composite materials that can be used in prosthetic joints.

BACKGROUND

The number of patients having spinal fusion surgery increased from 174,223 to 413,171 annually from 1998-2008. Damaged intervertebral discs (IVDs) of the spine can be fixed by replacing the disc with non-flexible material and then fusing the adjacent vertebrae using titanium plates, resulting in a lack of mobility at those joints. While this gives the patient relief over a shorter time span, over a longer time span the spinal discs of the adjacent vertebrae experience increased stress due to the lack of flexibility of the fused vertebrae. As a consequence, over time, the adjacent vertebrae and IVDs are often damaged as well.

One solution to preventing the development of adjacent segment disease is to preserve natural mobility by replacing fusion techniques with motion capable artificial discs. Artificial disc replacement has recently emerged as an alternative to fusion because the surgical procedure is safe and better preserves joint mobility. However, total disc replacement (TDR) rates for IVDs are low due to strict regulations for implant surgeries, demanding surgical techniques, low implant selection, and complications requiring surgery. A new cervical artificial (SECUR-C) metal disc that purports to maintain physiologic motion and thereby reduce the development of adjacent segment degeneration has just become available. Current TDR devices are composed of metal alloy plates sandwiching a plastic core, or a titanium mesh cage for bone infiltration that replaces the IVD, both of which can cause degeneration of relatively softer adjacent vertebrae and facets. One further concern about metal TDRs is they leach metal particles into blood circulation. The significance and potential impact of these circulating metal particles to the recipient of the TDR is not completely understood. Therefore, avoiding their circulation is desirable.

SUMMARY

Disclosed herein, in various aspects, is a synthetic material that can be used to form an implant. The synthetic material can comprise a plurality of rigid components, wherein each rigid component is spaced from each adjacent rigid component to define respective interstices between each rigid component and each adjacent rigid component. A flexible material can be disposed within each respective interstice and extend between and connect to adjacent rigid components.

The plurality of rigid components can cooperate to define a tessellation.

The plurality of rigid components can have hexagonal profiles.

The plurality of rigid components can have rectangular profiles.

The plurality of rigid components can have circular profiles.

The synthetic material can be formed in the shape of a vertebral disc.

The plurality of rigid components can each have a modulus of elasticity of at least 1 GPa.

The plurality of rigid components can each have a modulus of elasticity of between 1 and 2 GPa.

The plurality of rigid components can each have a modulus of elasticity of at least 2 GPa.

The flexible material can have a modulus of elasticity of about 1 MPa.

A prosthetic implant can comprise a synthetic material comprising a plurality of rigid components, wherein each rigid component is spaced from each adjacent rigid component to define respective interstices between each rigid component and each adjacent rigid component. A flexible material can be disposed within each respective interstice and extend between and connect to adjacent rigid components. The synthetic material can be formed in a shape having a circumferential wall and a hole defined within the circumferential wall.

The prosthetic implant can further comprise a viscoelastic core material within the hole defined by the circumferential wall.

The plurality of rigid components can each have a modulus of elasticity of at least 1 GPa.

The plurality of rigid components can each have a modulus of elasticity of between 1 and 2 GPa.

The plurality of rigid components can each have a modulus of elasticity of at least 2 GPa.

The flexible material can have a modulus of elasticity of about 1 MPa.

The viscoelastic core can have an elastic modulus of between 9 and 50 MPa.

A method can comprise 3D printing, with multi-material 3D printer, a synthetic material comprising: a plurality of rigid components, wherein each rigid component is spaced from each adjacent rigid component to define respective interstices between each rigid component and each adjacent rigid component; and a flexible material within each respective interstice and extending between and connected to adjacent rigid components.

The method can further comprise creating a prosthetic implant based on a medical image, wherein 3D printing the synthetic material comprises printing the synthetic material in a structure based on the medical image.

Creating the prosthetic implant can comprise using at least one processor to receive a medical image and modifying the medical image using 3D modeling software executed by the at least one processor.

BRIEF DESCRIPTION OF THE DRAWINGS

The accompanying drawings, which are incorporated in and constitute a part of this specification, illustrate several embodiments of the disclosed apparatus, system, and method and together with the description, serve to explain the principles of the disclosed apparatus, system, and method.

DETAILED DESCRIPTION

The present application can be understood more readily by reference to the following detailed description and appendix, which include examples, drawings, and claims. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an," and "the" include plural referents unless the context clearly dictates otherwise. Thus, for example, reference to "a tessera" can include two or more such tesserae unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Disclosed herein, in one aspect, are systems and methods for providing artificial tessellated implants. In exemplary uses, it is contemplated that the disclosed artificial tessellated implants can act as replacements for knee cartilage (meniscal replacement), intervertebral discs, and other joint structures.

Figure 1A:
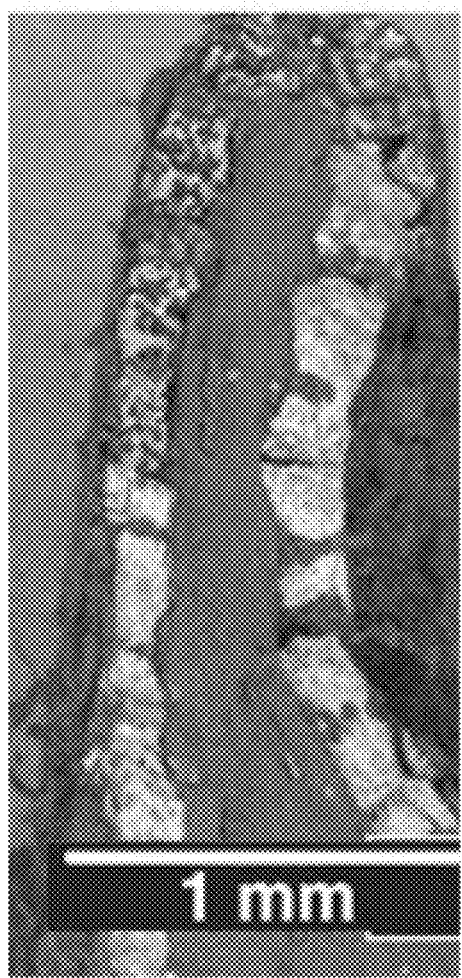
FIG. 1A is an image of a cross section of shark cartilage.
Figure 1B:
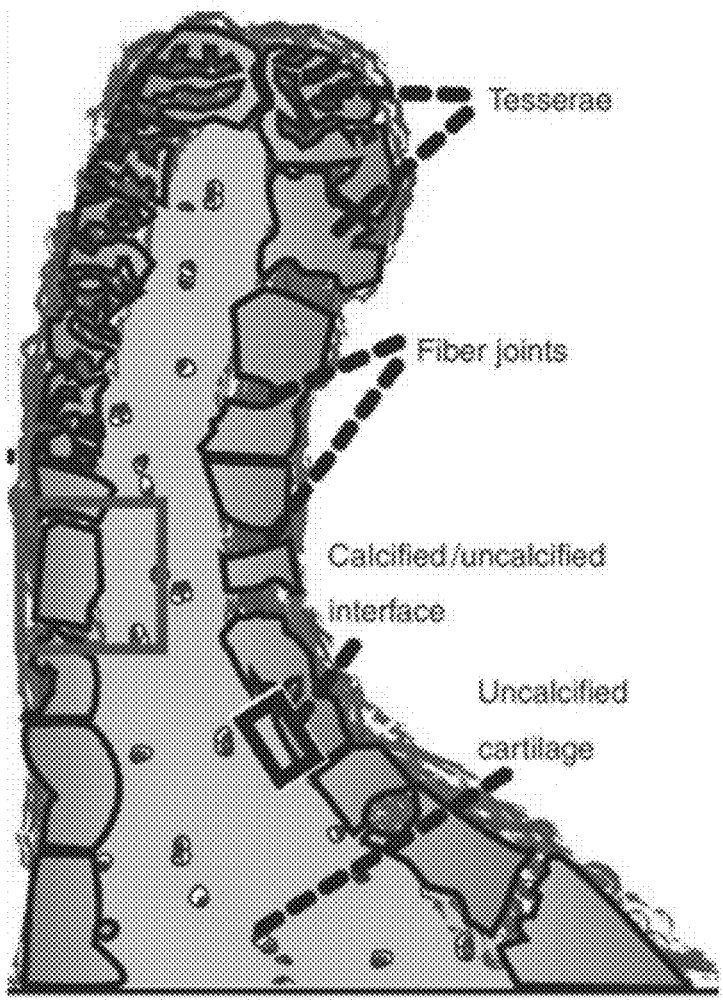
FIG. 1B is an illustration of the cross section of FIG. 1A with boundaries of certain components enhanced.

Thus, disclosed herein are systems and methods for providing artificial tessellated implants. In one aspect, disclosed is an implant comprising a plurality of discrete materials that form a composite material that is both stiff and flexible. Aspects of the material can be modeled after shark tessellated cartilage. FIG. 1A is an image of a cross section of shark cartilage, and FIG. 1B is an illustration of the cross section of FIG. 1A with lines to enhance boundaries of certain components. As shown, rigid tesserae are coupled to each other via fiber joints. The tesserae and fiber joints form a circumference around uncalcified cartilage.

Referring to FIG. 2, a material 100 (for preparing an artificial implant) can include a plurality of tesserae 102 (tesserae shaped structures) and intertesseral joints 104 positioned between respective tesserae. According to further aspects, the material can comprise a viscoelastic core as further disclosed herein. The viscoelastic core can form the general shape of the material. In exemplary aspects, the viscoelastic core can be at least partially circumferentially surrounded by the tesserae and intertesseral joints.

According to some optional aspects, the stiffness (i.e., E modulus) of the tesserae shaped structures can range from about 1 GPa to about 2 GPa. In some optional aspects, the material of the intertesseral joints can have a stiffness of about 1.0 MPa. In some embodiments, the viscoelastic core can be elastic and have a stiffness ranging from about 9 MPa to about 50 MPa. In further aspects, the viscoelastic core can have a stiffness ranging from about 1 MPa to about 3 MPa. The stiffness/elastic modulus of each material can be selected based on the type of implant (e.g., IVD spinal location, meniscus, etc.).

The material can be formed via multi-material 3D printing, using, for example, a Stratasys Connex3 Objet260 3D Printer. It is contemplated that the multi-material 3D printer can combine and grade between materials with different physical and/or optical properties to provide unprecedented ability to explore mechanics of composite materials, even those with a complex structure. The printed materials can be selected to have desired mechanical properties. The printed materials can further be medical-grade materials that are suitable for prosthetic implants. In some aspects, a polyjet technology can use twenty-two base resins that can be printed unblended or blended in pairs or trios. The modulus of elasticity for these materials can range from about 15 MPa to about 3500 MPa. Using the selectable material properties, the composite materials and structure disclosed herein can be formed. The materials can be biocompatible. For example, the materials may comprise silicone, acrylate, polycaprolactone (PCL), or various other materials depending on the application. Some optional materials include MED 610, provided by STRATASYS, and HT PCL 120K MG and 3D-Bioplotter Silicone TG, both provided by ENVISIONTEC. Optionally, MED 610 can be used for the viscoelastic core; 3D-Bioplotter Silicone TG can be used for the intertesseral joints; and HT PCL 120K MG can be used for the tesserae.

In comparison to 3D printing, conventional manufacturing technologies, which are often 'subtractive' (i.e. involving removal of material, as in drilling, milling, cutting) have limitations as to the structures that can be created at a cost-efficient basis. Certain structures can be formed in multi-step fabrication workflows, where composite phases are manufactured separately and combined, but these workflows can be restricted in their ability to combine materials into complex, integrated morphologies.

Figure 3B:
FIG. 3B illustrates a 3D mesh created from the medical image of FIG. 3A.
Figure 3A:
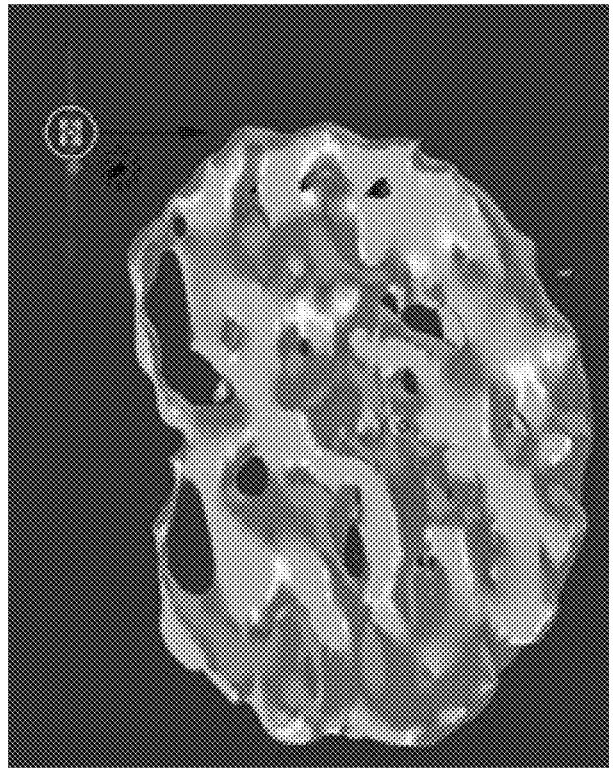
FIG. 3A is a medical image of a disc.

Using 3D printing, structures can be selected on an individual-by-individual basis. For example, medical imaging can be used to determine a desired size and shape for a prosthetic disc. FIG. 3A illustrates a medical image 200 of a disc. Referring to FIG. 3B, a 3D mesh 202 can be created from the medical image to define a volume that corresponds to the shape of the prosthetic disc. The 3D mesh can optionally be modified from the original medical image with 3D modeling software (e.g., SOLIDWORKS). FIG. 3B illustrates a mesh 202 that has been modified from the original medical image 200. The 3D mesh can optionally designate boundaries between separate materials. Further, portions of the mesh can be designated for certain materials. Thus, the tesserae can be distinguished from the intertesseral joints. Further, the portions of the 3D mesh designated to be the viscoelastic core can be distinguished and delineated in the 3D mesh. The 3D mesh can be provided to the 3D printer for printing.

Figure 4A:
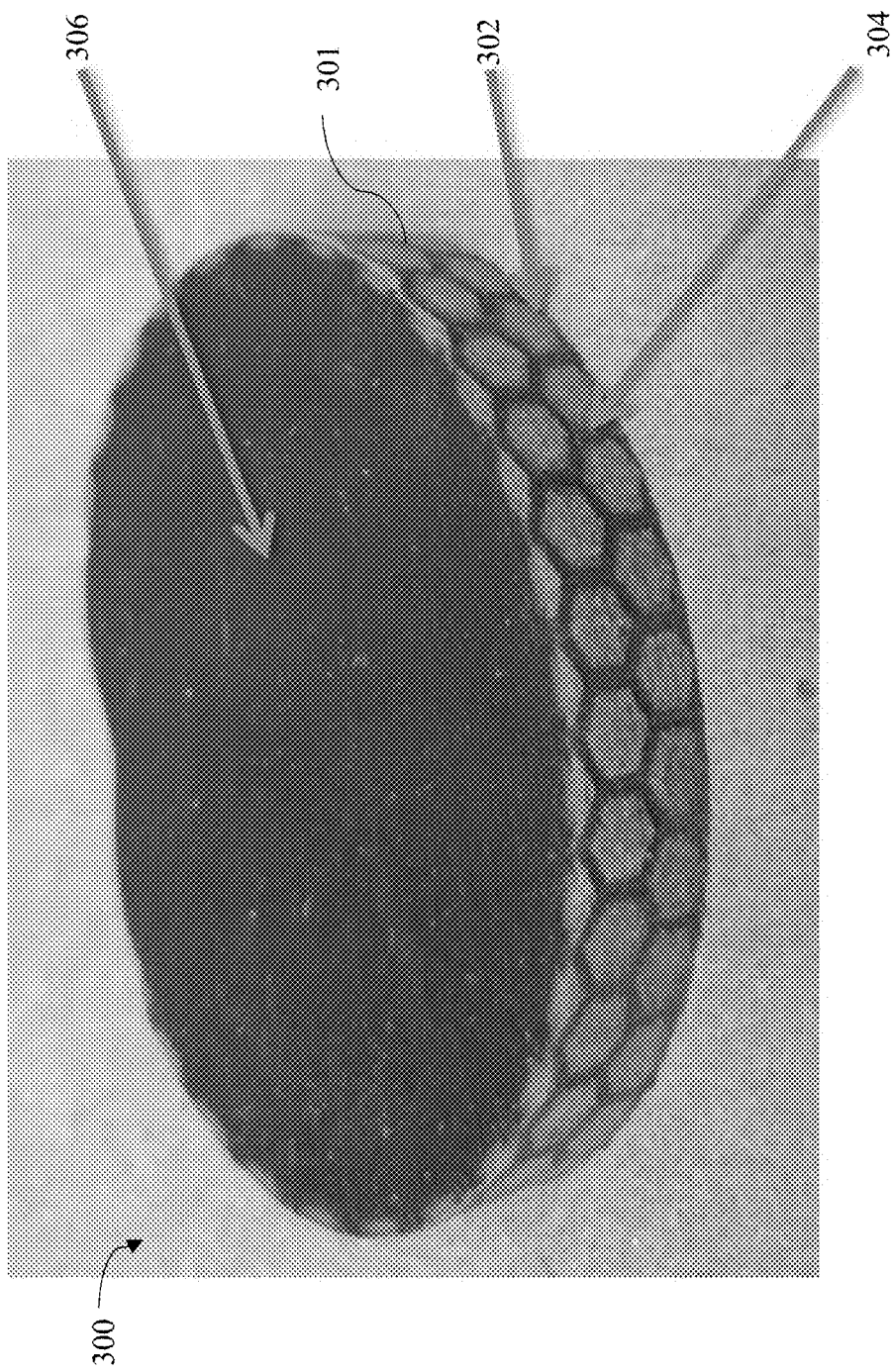
FIG. 4A is a perspective view of a prosthetic disc in accordance with embodiments disclosed herein.
Figure 4B:
FIG. 4B is a top view of the prosthetic disc of FIG. 4A.
Figure 4C:
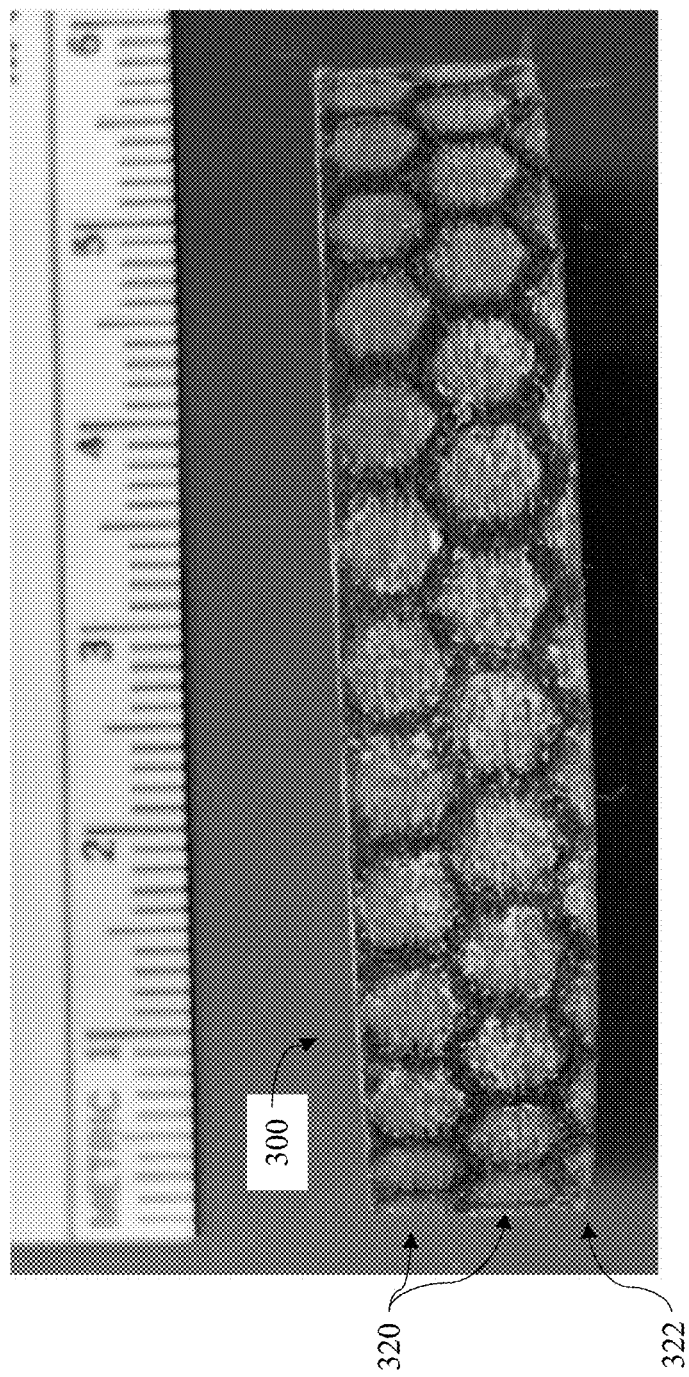
FIG. 4C is a side view of the prosthetic disc of FIG. 4A.
Figure 5:
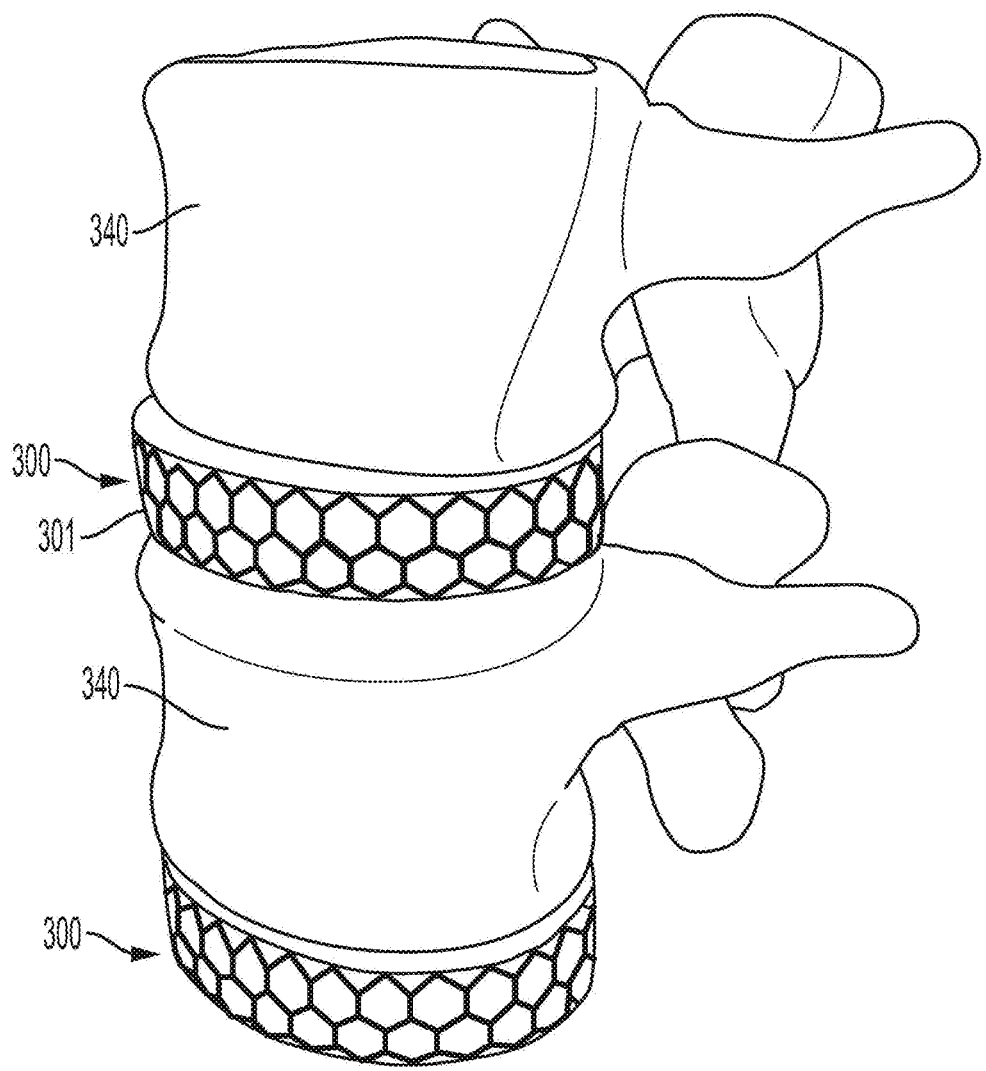
FIG. 5 is a perspective view of prosthetic discs positioned between replicas of vertebrae.
Figure 6A:
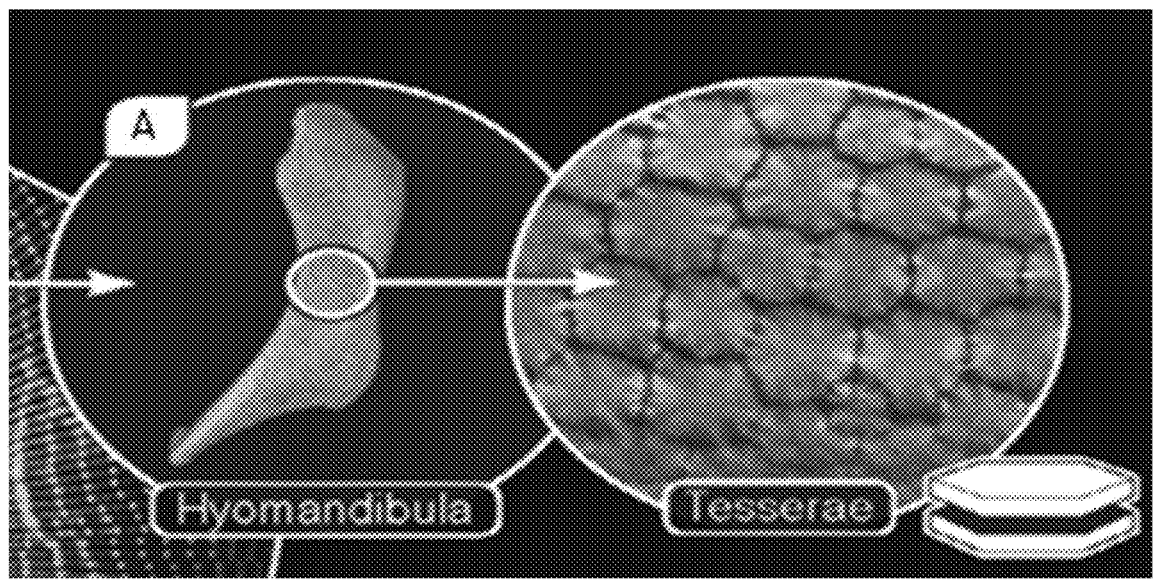
FIG. 6A illustrates a detailed view of tessellated cartilage found in the head and fins of sharks and rays.
Figure 6B:
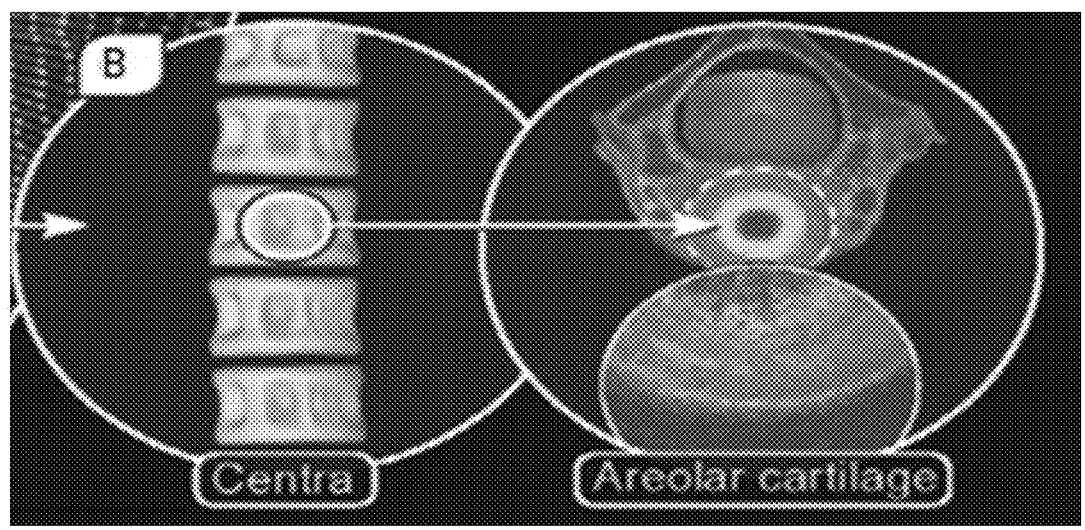
FIG. 6B illustrates areolar calcified cartilage located in the center of the vertebrae.
Figure 6C:
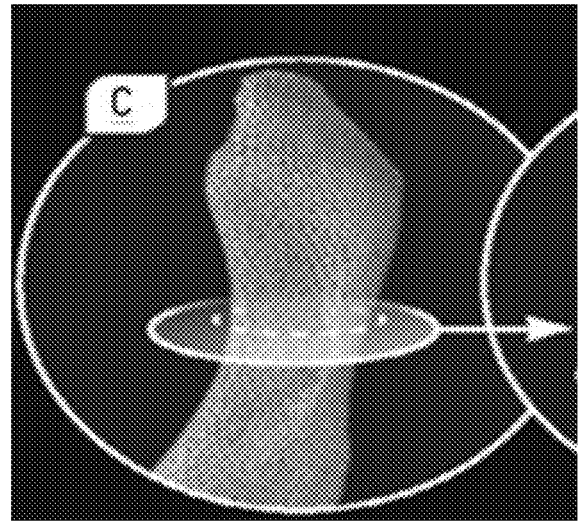
FIG. 6C illustrates a plane of a microCT cross section scan of the cartilage of FIG. 6A.
Figure 6D:
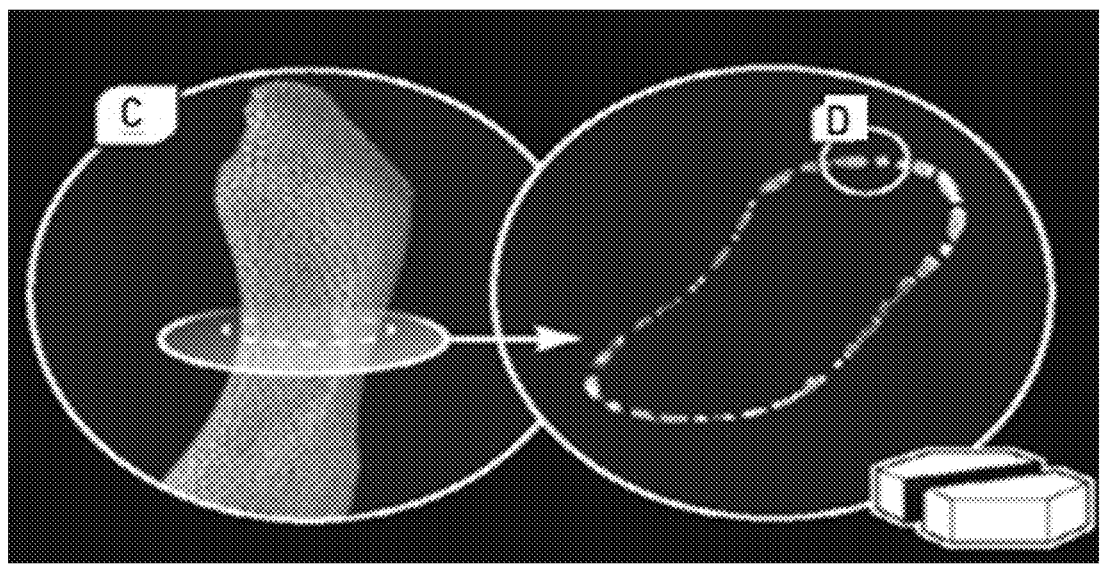
FIG. 6D illustrates a microCT cross-section of the skeleton showing only tesserae, taken in a plane perpendicular to the faces of the tesserae.
Figure 6E:
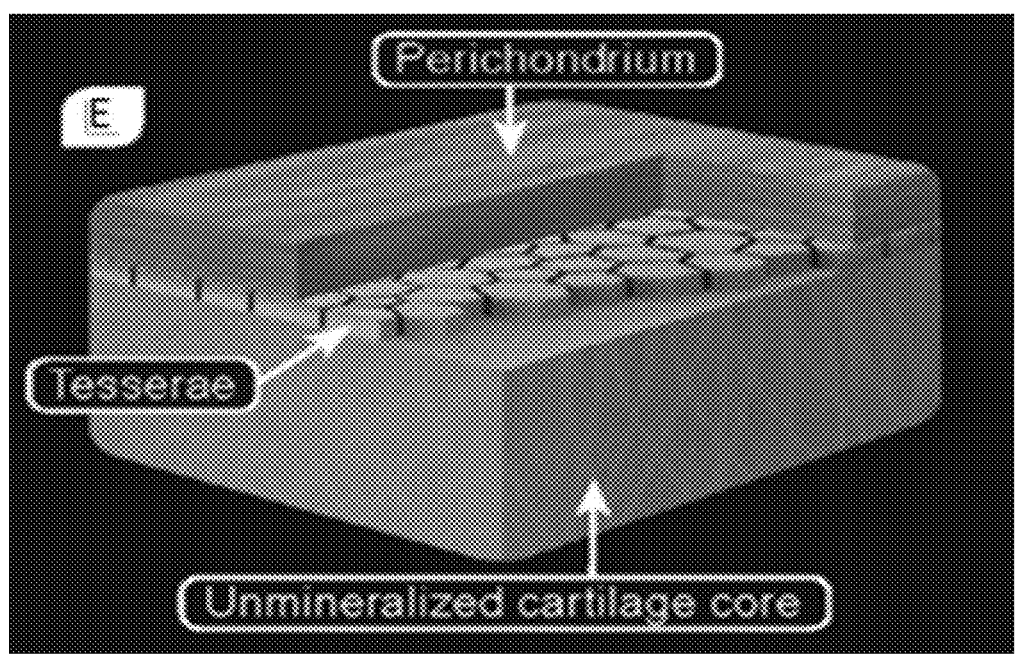
FIG. 6E illustrates a schematic of the tessellated cartilage organization.
Figure 7:
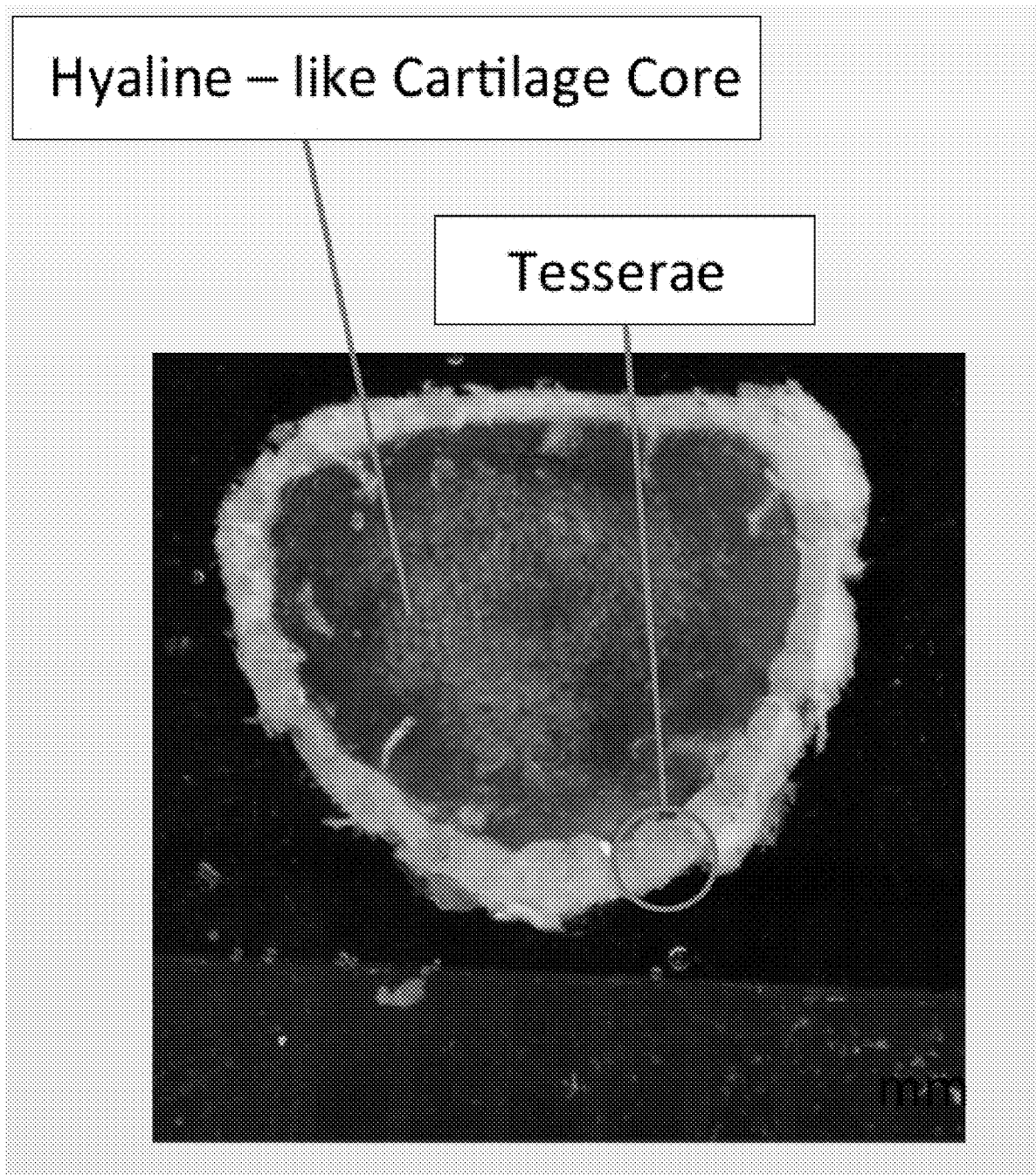
FIG. 7 illustrates a cross section of a tessellated cartilage portion of a shark.

Referring to FIGS. 4A-5, an implant (shown as a prosthetic disc) can be printed or otherwise fabricated. Although shown as a prosthetic disc, it is contemplated that other implant structures can be used. The prosthetic disc 300 can have a shape that corresponds to a healthy disc (e.g., a healthy intervertebral disc) of an individual. For example, the prosthetic disc 300 can have an oblong shape (e.g., an oval or generally oval shape). The disc 300 can further define an indentation 312. The indentation can be included to provide a location to receive blood vessels and/or nerves. The prosthetic disc 300 can comprise a material 301 comprising tesserae 302 that are separated by intertesseral joints 304. The material 301 can be formed or arranged to define a circumferential wall of the disc 300. The wall can define an opening 310 at a back side. The tesserae 302 can have hexagonal or generally hexagonal faces and can have a thickness (i.e., depth in a dimension perpendicular to the face of the tessera) of about five to fifty percent of the major dimension (e.g., the diagonal for hexagonal tesserae) of the face of the tesserae in a dimension perpendicular to the respective face of each tessera. The intertesseral joints 304 can optionally have the same thickness (in the same dimension) as the tesserae. Thus, the material 301 can have a thickness of about five to fifty percent of the major dimension of the tesserae. In further embodiments, the intertesseral joints 304 can have a thickness that is greater than or less than the thickness of the tesserae. In still further embodiments, some tesserae can have different thicknesses than other tesserae, and the thickness can be selected based on particular expected loading conditions for each given tessera. According to some optional aspects, the faces of the tesserae can each have a major dimension (e.g., a hexagonal diagonal) that is approximately five millimeters. Thus, the thickness of each tessera can be between about 0.25 mm to about 2.5 mm. Optionally, the thickness of each tessera can be from one to two millimeters. In further optional aspects, the tesserae can each have a major dimension of about two millimeters. In further aspects, the tesserae can have circular faces or rectangular faces.

As illustrated, each disc 300 can have a plurality of tesserae arranged in rows 320 that are parallel to the diameter of the disc (perpendicular to the vertical thickness of the disc). It is contemplated that the rows can be vertically stacked along the thickness of the disc. The disc 300 can comprise two rows, three rows, four rows, five rows, or more. Further, the disc 300 can have partial rows 322 that comprise portions of tesserae. Accordingly, the disc 300 can have fractional rows such as, for example, about 2.5 rows, about 3.5 rows, about 4.5 rows, etc. Thus, the disc 300 can have between two and three rows, between three and four rows, between four and five rows, or more. Optionally, in exemplary aspects, the tesserae of sequential rows can be circumferentially offset from one another. Optionally, the rows of tesserae can comprise two (or more) sets of alternating rows (i.e., every other row) of tesserae. For example, respective rows of a second set of alternating rows can be positioned vertically between sequential rows of a first set of alternating rows. In exemplary aspects, the rows of each set of alternating rows can have tesserae that are vertically aligned with one another, with the tesserae of rows of the other set(s) of alternating rows being circumferentially offset as further disclosed herein. Although described herein as being vertically stacked, it is understood that sequential rows of tesserae can include tesserae that vertically overlap (relative to a vertical axis) to produce a tessellated pattern as depicted in the drawings. Optionally, in exemplary aspects, the tesserae within a single row can be evenly circumferentially spaced form one another.

The prosthetic disc 300 can further comprise a viscoelastic core 306. The viscoelastic core 306 can comprise a medical grade material. The viscoelastic core 306 can fill the space within the wall. It is contemplated that the viscoelastic core 306 can optionally have a constant thickness across the disc so that the disc has a prism shape.

It is contemplated that the prosthetic disc 300 can have a select shape based on the vertebrae it is to be disposed between so that the vertebrae 340 positioned above and below the can engage the material 301 to bias against and load the material 301 in a direction perpendicular to its thickness.

Figure 10:
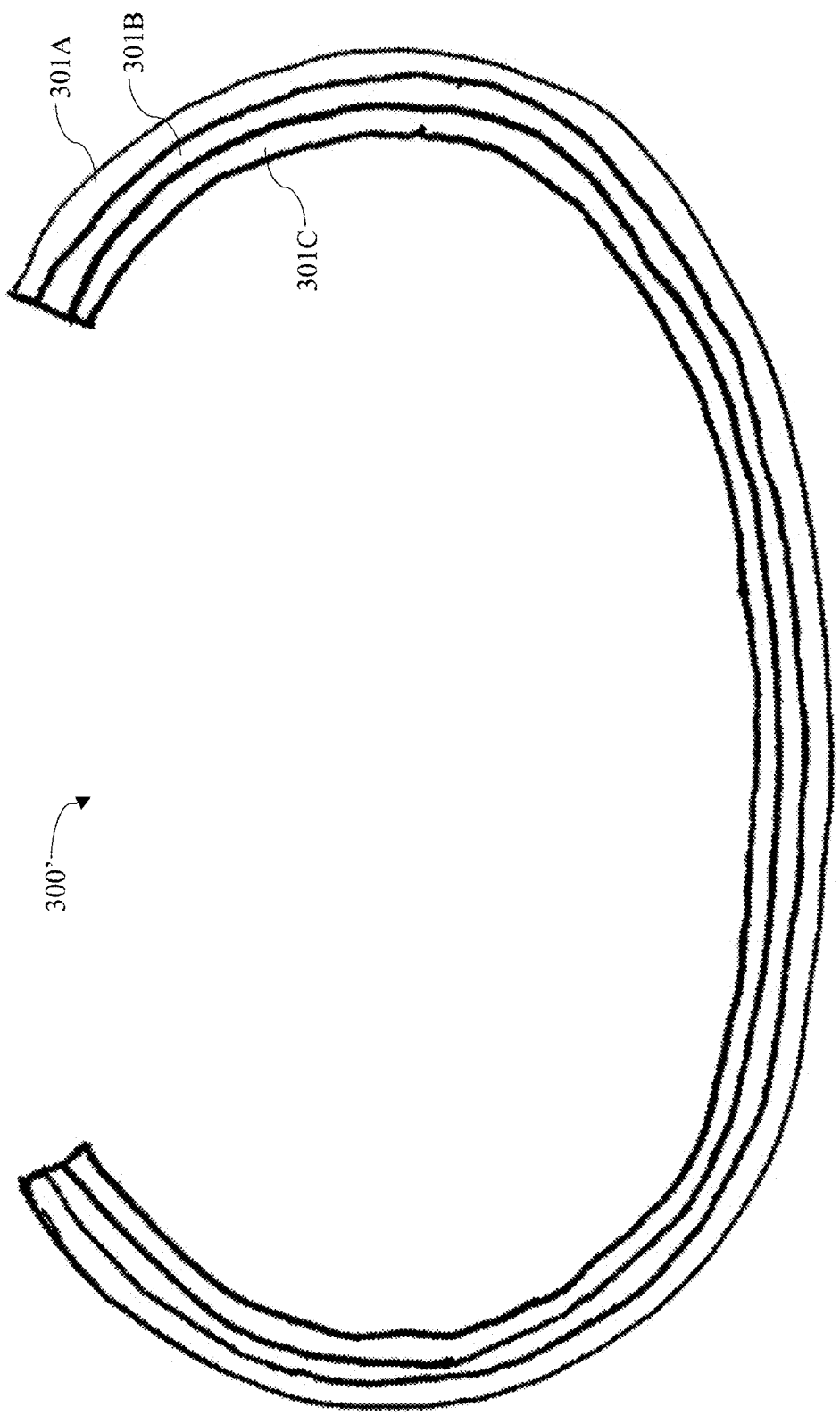
FIG. 10 is a top view of a prosthetic disc including a plurality of stacked material layers.

Referring to FIG. 10, according to some aspects, a prosthetic can include a plurality of material layers, each material layer comprising tesserae and intertesseral joints. The plurality of material layers can be arranged along the depth dimension of the material layers, with the plurality of layers cooperating to define a wall of the implant. Thus, for a disc, the material layers can be concentrically stacked (in a radial direction). For example, a prosthetic disc 300' can comprise a first material layer 301A, a second material layer 301B, and a third material layer 301C. It is contemplated that the arrangement of the tesserae (e.g., the orientation of the tesserae and the corresponding angle of the rows of tesserae)

can affect the material properties (e.g., elastic modulus) in a given dimension. Thus, in some optional aspects, each layer can be angularly offset from each adjacent layer. For example, the tesserae of the first material layer 301A can be rotated with respect to the orientation of the tesserae of the second material layer 301B. Optionally, the tesserae can be rotated by about thirty degrees with respect to tesserae of adjacent layers. In further embodiments, the tesserae (and, thus, their corresponding direction of row orientation) can be rotated by between zero and sixty degrees, or between fifteen and forty-five degrees, or between zero and ninety degrees, or between thirty and sixty degrees, or between fifty and sixty degrees.

It is contemplated that an exemplary prosthetic disc can withstand up to 100 MPa of pressure. In further aspects, the mechanical properties of the prosthetic can be selected based on the size and weight of the individual receiving the disc or the position of the prosthetic within the individual. It is contemplated that the prosthetic implant can be configured to allow strain of up to 10% in compression and tension. In exemplary aspects, it is contemplated that a prosthetic disc as disclosed herein can have a compressive stiffness of at least 20 MPa. It is further contemplated that a prosthetic disc as disclosed herein can have a tensile stiffness of at least 3 MPa. It is further contemplated that the prosthetic can accommodate twenty degrees of motion (e.g., pivoting of the upper surface with respect to the lower surface) when the prosthetic is subject to torsion.

It is contemplated that devices, systems, and methods disclosed herein can provide an artificial implant that can be used as replacements for intervertebral discs and knee cartilage. It is further contemplated that the disclosed devices can allow flexion rather than fusion at the joint, leading to less degradation of adjacent discs and bones.

The following non-limiting examples provide details of particular embodiments of the disclosed materials and implants.

Example 1

Figure 2A:
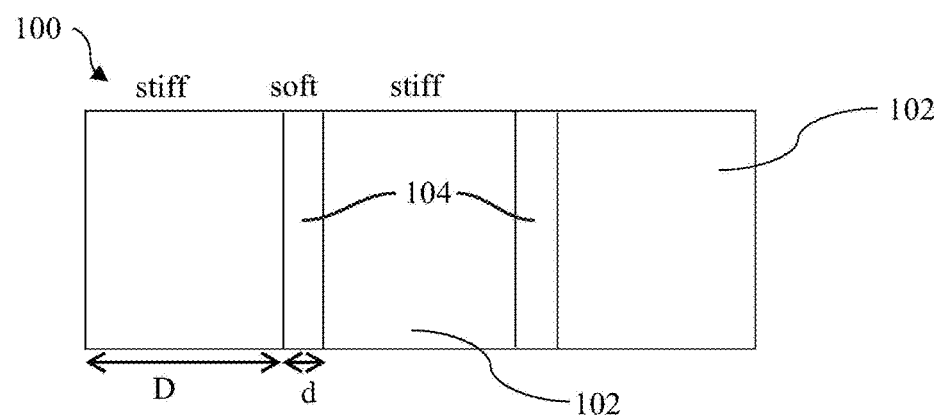
FIG. 2A is a schematic of a tessellated composite material in accordance with embodiments disclosed herein.
Figure 2B:
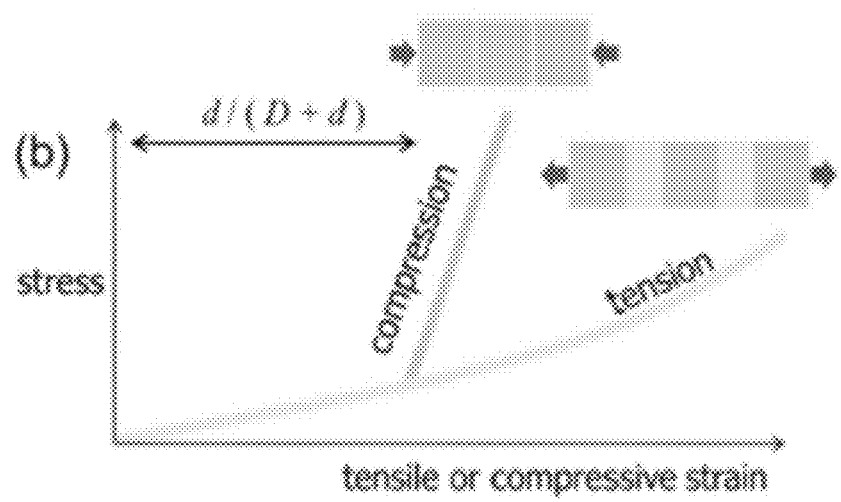
FIG. 2B is a predicted stress-strain curve for compression and for tension of the tessellated composite material of FIG. 2A.
Figure 2C:
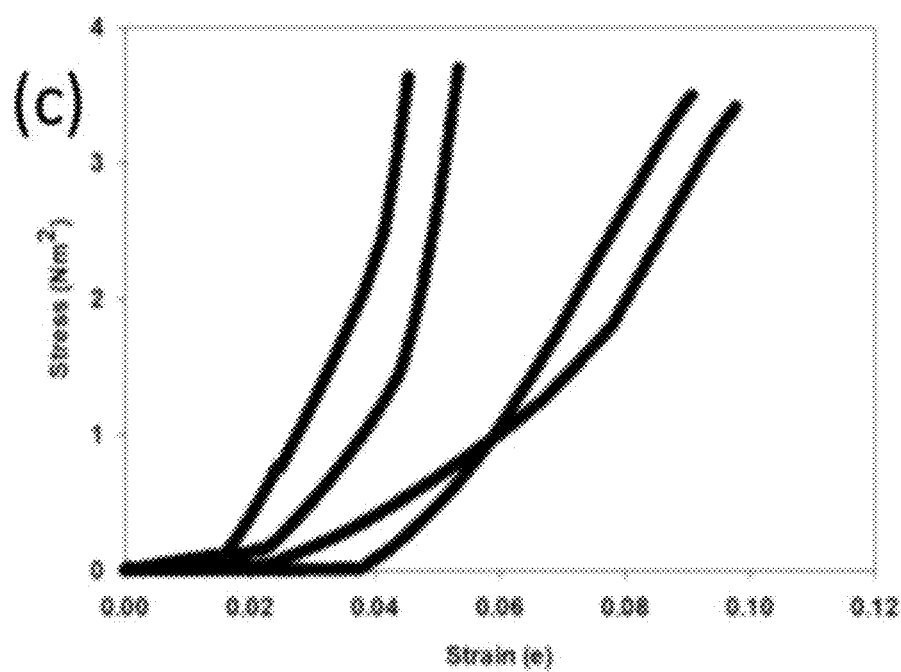
FIG. 2C illustrates measured stress-strain curves of shark tessellated cartilage in compression and tension.

The disclosed material and structures formed from the material (e.g., prostheses) can comprise certain aspects of shark and ray skeletons. Referring to FIGS. 6A-6E and 7, shark and ray skeletons predominantly comprise a unique type of cartilage, called tessellated cartilage, setting them apart from the vast majority of other vertebrates with skeletons of bone. Despite this, many of these fishes have extremely demanding ecologies, being capable of large body sizes, swimming at astounding speeds, and biting through or crushing prey with skeletons much harder than cartilage. The unique structure of tessellated cartilage can help to enable such performance. The core of the skeletal element comprises hyaline-like cartilage, similar to that in most other vertebrates, which is sheathed in a layer of minute mineralized tiles interconnected by elastic ligaments. The composite nature of this skeleton, comprising both flexible, viscoelastic, and stiff tissues in discrete locations, can confer resistance to fracture while promoting slight bending. It is further contemplated that some regions of the skeleton are able to stiffen locally under increased compressive force while other regions of the same element are able to undergo tensile stretching, much like what occurs within an intervertebral disc (IVD) when a human bends. Referring to FIG. 2A, tessellated materials can comprise alternating soft (i.e. ligaments in tessellated cartilage) and stiff (i.e. tesserae in tessellated cartilage) parts. Referring also to FIG. 2B, the predicted stress-strain curve of a tessellated material looks similar when loaded in compression and tension up to an inflection point. Then, once the stiff material comes closer under further compressive load, the material is predicted to become stiffer. In contrast, the softer material can continue to behave in an elastic manner under tension. FIG. 2C illustrates measured stress-strain curves of shark tessellated cartilage in compression and tension.

Example 2

Prosthetic discs in accordance with embodiments of the present disclosure can be configured to mimic or exceed the structural and mechanical properties of a human IVD while avoiding features that cause problems (e.g., herniated discs). The human IVD is evolved to serve its purpose between vertebrae to give a bipedal upright human spine optimum motion, stability and durability. The human IVD comprises three components: tough outer rings of annular fibers known collectively as the annulus fibrosus (AF), a gelatinous center known as the nucleus pulposus (NP), and capped above and below with relatively flat, averaging 1 mm thick, discs of cartilage known as cartilaginous end plates (CEPs) sandwiching the AF and NP in between a top and a bottom CEP. The annulus fibrosus (AF) primarily comprises fibrils formed in multiple concentric rings. These multiple rings can form a lamellar structure of the disc (AF) with layers of fibers at alternating angles to one another. These angles vary but are often seen at 50-60+ degrees to each adjacent layer. The annular fibers are primarily elastic and are connected sparsely to the adjacent layers, inner and outer with other elastic fibers. The AF serves to contain the NP and attach securely via elastic fibrils into the vertebral bodies above and below to respond to torsion, compression and tensile forces. Because the concentric rings do not fully form complete circles, there are weaknesses posteriorly and posterolaterally that make these areas susceptible to herniation, fissures and failure. The nucleus pulposus is primarily a gelatinous material in the center of the AF. Because the NP has fluid properties, it is not compressible without expansion. When the human spine experiences an axial load, the fluid properties can be compressed downward from the vertebra above onto the disc then onto the vertebra below. This then compresses the NP outwardly in other directions, thereby expanding the elastic fibers of the AF. The NP can comprise cartilaginous components to support compression forces and proteoglycan components to retain water content. The line between the NP and AF is more transitional than was originally expected (i.e. transition zone, TZ). The cartilaginous end plates cap the vertebral bodies above and below the human disc and serve to contain the AF and NP and to adhere the disc complex to the vertebral bodies via perforating Sharpey's fibers. CEPs can be dynamic, believed to be semi-permeable to allow nutrients and water to imbibe into the NP more in the center than the edges. The can degenerate and change with age. These three components, the AF, the NP and the CEPs are integrated to function as a unit with the vertebrae above and below forming a spinal unit also known as a motion unit that can tolerate combinations of flexion, extension, lateral bending, and rotation of the spine at varying amounts at each level of the human spine.

The NP can be primarily responsible for the elastic properties of the IVD, but all components contribute significantly. The compressive stiffness (E modulus: 19.5±4.1 MPa in 28±8 year old persons and 10.6±3.4 MPa in 70±7 year old persons) of the healthy IVD is 6-7 times higher than the tensile stiffness (E modulus: 2.9±0.8 MPa in 28±8 year old persons and 1.7±1 MPa in 70±7 year old persons 3.3±2.1 MPa). Stiffness of the spine can vary depending on the spinal region. The loading of the IVD measured during normal activities was 0.1-0.5 MPa, and increased up to 2.3 MPa during lifting 20 kg weight. Studies on sheep IVDs show increased stiffness of IVD after cycled loading, which fully recovered after a period of unloading.

IVDs in the human spine differ in design and function just as vertebrae vary by spinal region. Human IVDs within the same region also differ from person to person. A replacement IVD can, therefore, optionally be custom-designed in advance for the region, vertebral motion unit and individual properties that best match that which it is to replace. For example, in flexion and extension of the lumbar spine, anterior translation of one vertebra on the other should be 8% or less while posterior translation should be 9% or less. Translation exceeding this is known as alteration of motion segment integrity (AOMSI). Additionally, angular motion of one lumbar vertebra to adjacent vertebra should allow no greater than 15 degrees difference within the first 3 lumbar units, L1/L2, L2/L3 or L3/L4 or no more than 20 degrees at L4/L5 and 25 degrees at L5/S1 (Rondinelli, 2008). Desirable properties of replacement discs can vary depending on patient age and spinal location and can, accordingly, be selected based on the patient age and spinal location.

Example 3

Material properties and structures in accordance with embodiments disclosed herein can be selected from material properties and structures of tessellated cartilage from sharks and rays.

Referring to FIGS. 6A-6E and 7, shark and ray uncalcified cartilage can be compositionally similar to human hyaline cartilage and suggests that it can be at least as stiff, if not several orders of magnitude stiffer for similar loading rates (E-Modulus mammalian: 0.45-19 MPa vs. shark/ray: 2-775 MPa). In contrast, tesserae have been demonstrated by nanoindentation to be several orders of magnitude stiffer similar in stiffness to the cancellous bone of mammals.

It is conventionally understood that covering a cartilage-like gel with a hard, continuous shell is expected to increase the stiffness but decrease the flexibility of a composite. However, embodiments disclosed herein, comprising a tessellated shell with interacting tiles, can maximize desirable properties of both tissue phases. For example, it can be shown that compared with embryonic (non-tessellated) small-spotted catsharks, adult individuals have jaw cartilage that has a higher ability to damp mechanical energy, but it is also stiffer. A large portion of the stiffness can be attributed to the tessellated layer in adult animals. From the biological perspective, this change in properties can permit adults to consume harder prey than newborns. These material properties can be engineering considerations, since stiffness and damping are typically negatively correlated in manmade materials.

Mechanical tests of whole tessellated skeletal elements can provide a wide range of mechanical properties with considerable variation between different cartilage elements (jaws: 40-350 MPa, propterygium: 140-2,500 MPa) and species. Shape and mineralization (20-70%) of the overall cartilage elements can vary widely and can impact the stiffness of the element. Variation in stiffness can be a function of the complex geometry of the tessellation, as tissue properties can be heavily dependent on tesserae geometry, the orientation of the tessellation relative to loading direction, and the thickness of the tessellated layer. Stiffness of whole cartilaginous elements can vary among species from 159-651 MPa, and corresponds to mineralization (% of cross section), 19-61%. For example, tessellated cartilage cubes from blue sharks loaded normal to the tesseral mat (in stress relaxation experiments) behave similarly to non-tessellated cubes, being ~45 times softer than tessellated cubes with the load applied in-plane with the tesseral mat. Additionally, the properties of tessellate cartilage elements apparently depend on the species and the skeletal element tested.

Example 4

Figure 8:
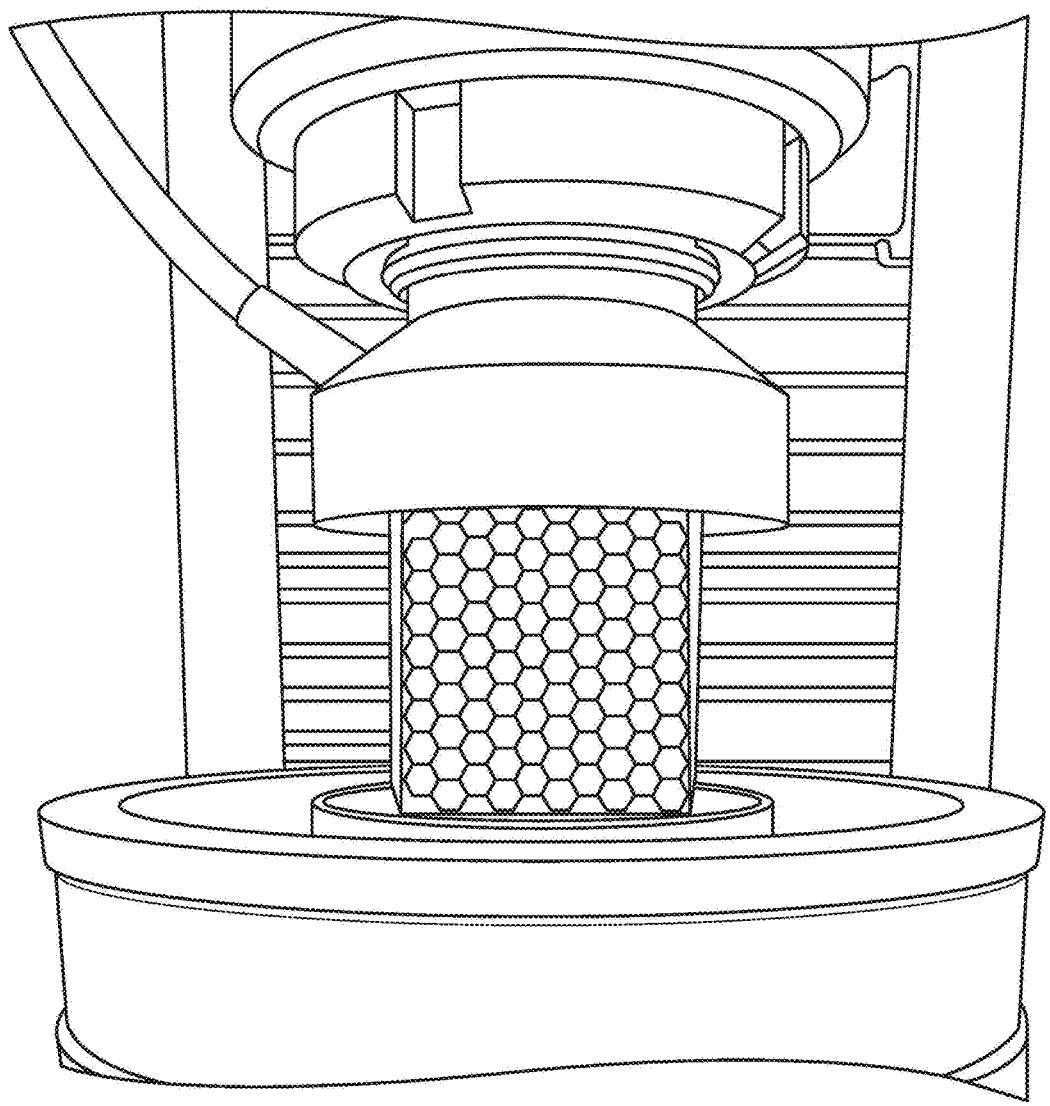
FIG. 8 illustrates a 3D printed synthetic tessellated composite material cube being tested in a stress-strain test apparatus.
Figure 9:
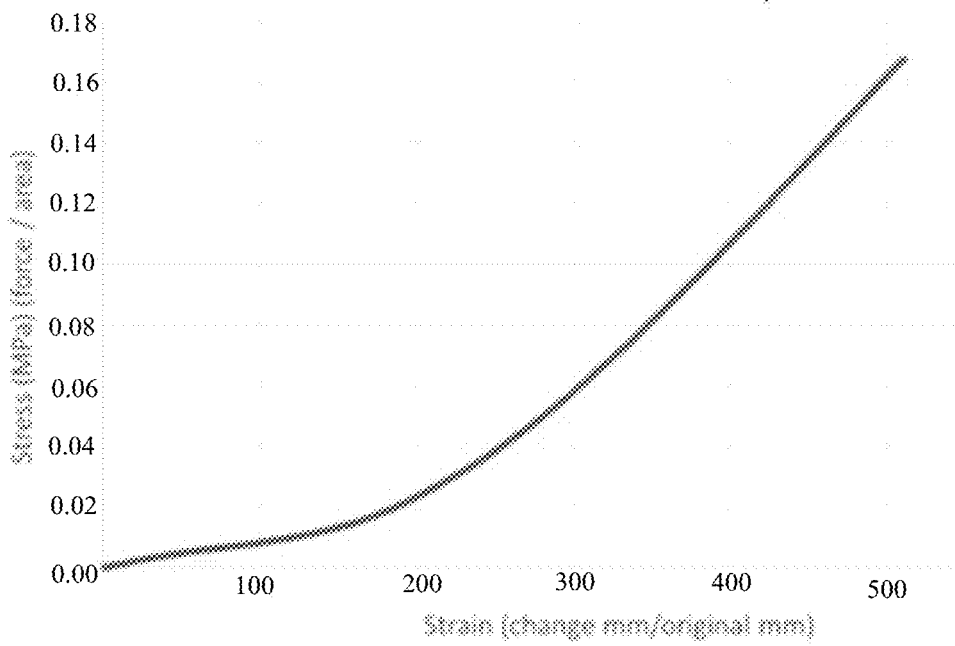
FIG. 9 illustrates a comparison between the stress-strain curve of a lower jaw specimen of a mako shark and the stress-strain curve of the 3D printed synthetic tessellated composite material cube of FIG. 8.
Figure 9:
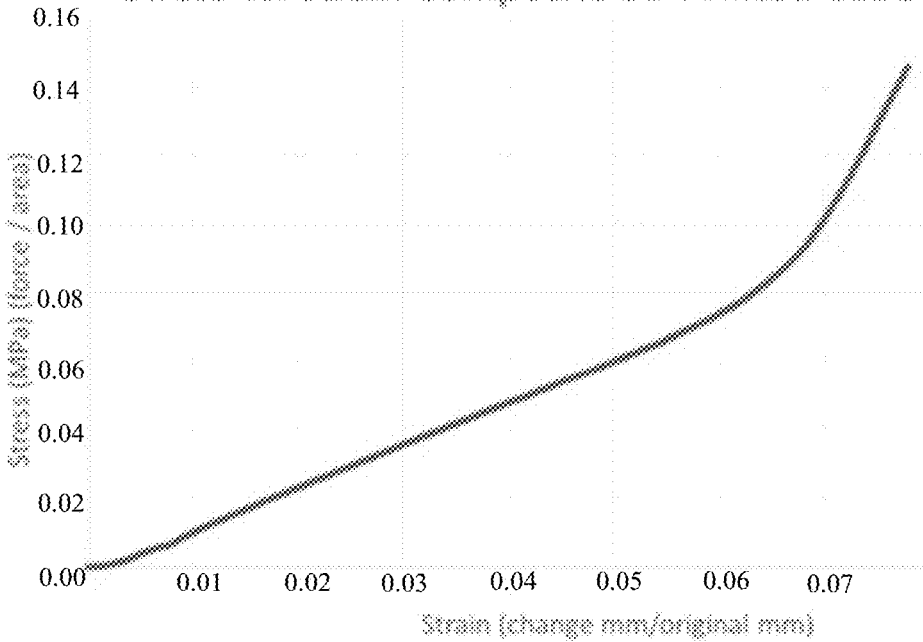

Referring to FIGS. 8 and 9, a 3D printed synthetic tessellated material was tested in a test apparatus and compared to a mako shark jaw portion. The results indicate similar profiles in stress-strain curves of the respective materials.

Exemplary Aspects

In view of the described device, systems, and methods and variations thereof, herein below are certain more particularly described aspects of the invention. These particularly recited aspects should not, however, be interpreted to have any limiting effect on any different claims containing different or more general teachings described herein, or that the "particular" aspects are somehow limited in some way other than the inherent meanings of the language literally used therein.

Aspect 1: A synthetic material comprising: a plurality of rigid components, wherein each rigid component is spaced from each adjacent rigid component to define respective interstices between each rigid component and each adjacent rigid component; and a flexible material within each respective interstice and extending between and connected to adjacent rigid components.

Aspect 2: The synthetic material of aspect 1, wherein the plurality of rigid components cooperate to define a tessellation.

Aspect 3: The synthetic material of aspect 2, wherein the plurality of rigid components have hexagonal profiles.

Aspect 4: The synthetic material of aspect 2, wherein the plurality of rigid components have rectangular profiles.

Aspect 5: The synthetic material of aspect 2, wherein the plurality of rigid components have circular profiles.

Aspect 6: The synthetic material of any one of the preceding aspects, wherein the synthetic material is formed in the shape of a vertebral disc.

Aspect 7: The synthetic material of any one of the preceding aspects, wherein the plurality of rigid components each have a modulus of elasticity of at least 1 GPa.

Aspect 8: The synthetic material of aspect 7, wherein the plurality of rigid components each have a modulus of elasticity of between 1 and 2 GPa.

Aspect 9: The synthetic material of aspect 7, wherein the plurality of rigid components each have a modulus of elasticity of at least 2 GPa.

Aspect 10: The synthetic material of any one of the preceding aspects, wherein the flexible material has a modulus of elasticity of about 1 MPa.

Aspect 11: A prosthetic implant comprising: a synthetic material comprising: a plurality of rigid components, wherein each rigid component is spaced from each adjacent rigid component to define respective interstices between each rigid component and each adjacent rigid component; and a flexible material within each respective interstice and extending between and connected to adjacent rigid components, wherein the synthetic material is formed in a shape having a circumferential wall and a hole defined within the circumferential wall.

Aspect 12: The prosthetic implant of aspect 11, further comprising a viscoelastic core material within the hole defined by the circumferential wall.

Aspect 13: The prosthetic implant of aspect 11 or aspect 12, wherein the plurality of rigid components each have a modulus of elasticity of at least 1 GPa.

Aspect 14: The prosthetic implant of aspect 13, wherein the plurality of rigid components each have a modulus of elasticity of between 1 and 2 GPa.

Aspect 15: The prosthetic implant of aspect 13, wherein the plurality of rigid components each have a modulus of elasticity of at least 2 GPa.

Aspect 16: The prosthetic implant of any one of aspects 9-15, wherein the flexible material has a modulus of elasticity of about 1 MPa.

Aspect 17: The prosthetic implant of aspect 10, wherein the viscoelastic core has an elastic modulus of between 9 and 50 MPa.

Aspect 18: A method comprising: 3D printing, with multi-material 3D printer, a synthetic material comprising: a plurality of rigid components, wherein each rigid component is spaced from each adjacent rigid component to define respective interstices between each rigid component and each adjacent rigid component; and a flexible material within each respective interstice and extending between and connected to adjacent rigid components.

Aspect 19: The method of aspect 18, further comprising: creating a prosthetic implant based on a medical image, wherein 3D printing the synthetic material comprises printing the synthetic material in a structure based on the medical image.

Aspect 20: The method of aspect 19, wherein creating the prosthetic implant comprises: using at least one processor to receive a medical image; and modifying the medical image using 3D modeling software executed by the at least one processor.

Although several embodiments of the invention have been disclosed in the foregoing specification and the following appendices, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A synthetic material comprising:
a plurality of rigid components, each rigid component of the plurality of rigid components having a length, wherein, along the length of each rigid component of the plurality of rigid components, said rigid component is spaced from each other rigid component of the plurality of rigid components, wherein each rigid component of the plurality of rigid components is spaced from each adjacent rigid component of the plurality of rigid components to define respective interstices between each rigid component and each adjacent rigid component; and a flexible material within each respective interstice and extending between and connected to adjacent rigid components of the plurality of rigid components,
wherein at least one rigid component of the plurality of rigid components has an outer perimeter, wherein the flexible material continuously surrounds and contacts the outer perimeter of the at least one rigid component.

2. The synthetic material of claim 1, wherein the plurality of rigid components cooperate to define a tessellation.

3. The synthetic material of claim 2, wherein the plurality of rigid components have hexagonal cross-sectional profiles.

4. The synthetic material of claim 2, wherein the plurality of rigid components have rectangular cross-sectional profiles.

5. The synthetic material of claim 2, wherein the plurality of rigid components have circular cross-sectional profiles.

6. The synthetic material of claim 1, wherein the synthetic material is formed in the shape of a vertebral disc.

7. The synthetic material of claim 1, wherein the plurality of rigid components each have a modulus of elasticity of at least 1 GPa.

8. The synthetic material of claim 7, wherein the plurality of rigid components each have a modulus of elasticity of between 1 and 2 GPa.

9. The synthetic material of claim 7, wherein the plurality of rigid components each have a modulus of elasticity of at least 2 GPa.

10. A prosthetic implant comprising:
a synthetic material comprising:
a plurality of rigid components, each rigid component of the plurality of rigid components having a length, wherein, along the length of each rigid component of the plurality of rigid components, said rigid component is spaced from each other rigid component of the plurality of rigid components, wherein each rigid component of the plurality of rigid components is spaced from each adjacent rigid component of the plurality of rigid components to define respective interstices between each rigid component and each adjacent rigid component; and
a flexible material within each respective interstice and extending between and connected to adjacent rigid components of the plurality of rigid components,
wherein at least one rigid component of the plurality of rigid components has an outer perimeter, wherein the flexible material continuously surrounds and contacts the outer perimeter of the at least one rigid component,
wherein the synthetic material is formed in a shape of a circumferential wall, wherein the circumferential wall defines an axial hole therethrough.

11. The prosthetic implant of claim 10, further comprising a viscoelastic core material within the hole defined by the circumferential wall.

12. The prosthetic implant of claim 10, wherein the plurality of rigid components each have a modulus of elasticity of at least 1 GPa.

13. The prosthetic implant of claim 12, wherein the plurality of rigid components each have a modulus of elasticity of between 1 and 2 GPa.

14. The prosthetic implant of claim 12, wherein the plurality of rigid components each have a modulus of elasticity of at least 2 GPa.

15. The prosthetic implant of claim 10, wherein the flexible material has a modulus of elasticity of about 1 MPa.

16. A method comprising:
3D printing, with multi-material 3D printer, a synthetic material comprising:
- a plurality of rigid components, each rigid component of the plurality of rigid components having a length, wherein, along the length of each rigid component of the plurality of rigid components, said rigid component is spaced from each other rigid component of the plurality of rigid components, wherein each rigid component of the plurality of rigid components is spaced from each adjacent rigid component of the plurality of rigid components to define respective interstices between each rigid component and each adjacent rigid component; and
- a flexible material within each respective interstice and extending between and connected to adjacent rigid components of the plurality of rigid components,
- wherein, after 3D printing, at least one rigid component of the plurality of rigid components has an outer perimeter, wherein the flexible material continuously surrounds and contacts the outer perimeter of the at least one rigid component.

17. The synthetic material of claim 1, wherein the plurality of rigid components are arranged in rows.

18. The prosthetic implant of claim 10, wherein the plurality of rigid components are arranged in rows.

19. The prosthetic implant of claim 10, wherein the circumferential wall defines a circumferential outer surface of the prosthetic implant, and wherein the plurality of rigid components define at least a portion of the circumferential outer surface of the prosthetic implant.

20. The synthetic material of claim 1, wherein the synthetic material defines a first stress-strain curve to an inflection, wherein the synthetic material defines a second stress-strain curve beyond the inflection, wherein the synthetic material defines a second stress-strain curve beyond the inflection, and wherein the second stress-strain has a greater slope than a slope of the first stress-strain curve.

* * * * *